(12) United States Patent
Nyberg

(10) Patent No.: US 9,650,609 B2
(45) Date of Patent: *May 16, 2017

(54) BIOARTIFICIAL LIVER SYSTEM

(71) Applicant: Mayo Foundation for Medical Education and Research, Rochester, MN (US)

(72) Inventor: Scott L. Nyberg, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 43 days.

This patent is subject to a terminal disclaimer.

(21) Appl. No.: 14/307,039

(22) Filed: Jun. 17, 2014

(65) Prior Publication Data

US 2014/0295548 A1  Oct. 2, 2014

Related U.S. Application Data

(63) Continuation of application No. 11/562,008, filed on Nov. 21, 2006, now Pat. No. 8,785,117, which is a continuation of application No. 10/164,817, filed on Jun. 7, 2002, now Pat. No. 7,160,719.

(51) Int. Cl.
| | | |
|---|---|---|
| *C12N 5/07* | (2010.01) | |
| *C12N 5/071* | (2010.01) | |
| *A61M 1/34* | (2006.01) | |
| *B01D 63/02* | (2006.01) | |

(52) U.S. Cl.
CPC .......... *C12N 5/067* (2013.01); *A61M 1/3472* (2013.01); *A61M 1/3489* (2014.02); *B01D 63/02* (2013.01); *B01D 2313/50* (2013.01)

(58) Field of Classification Search
CPC .................................................. C12N 5/067
See application file for complete search history.

(56) References Cited

U.S. PATENT DOCUMENTS

| | | |
|---|---|---|
| 3,129,066 A | 4/1964 | Ambrogi |
| 4,336,329 A | 6/1982 | Hesse et al. |
| 4,639,422 A | 1/1987 | Geimer |
| 4,647,539 A | 3/1987 | Bach |
| 4,804,628 A | 2/1989 | Cracauer et al. |
| 5,202,254 A | 4/1993 | Amiot et al. |
| 5,270,192 A | 12/1993 | Li et al. |
| 5,270,207 A | 12/1993 | Matsumura et al. |
| 5,328,614 A | 7/1994 | Matsumura |
| 5,523,228 A | 6/1996 | Ingram et al. |
| 5,595,909 A | 1/1997 | Hu et al. |
| 5,605,835 A | 2/1997 | Hu et al. |
| 5,624,839 A | 4/1997 | Yada et al. |
| 5,654,197 A | 8/1997 | Jem |
| 5,658,797 A | 8/1997 | Bader |
| 5,981,211 A | 11/1999 | Hu et al. |
| 6,048,727 A | 4/2000 | Kopf |
| 6,096,544 A | 8/2000 | Bramble et al. |
| 6,190,913 B1 | 2/2001 | Singh |
| 6,218,182 B1 | 4/2001 | Naughton et al. |
| 6,228,607 B1 | 5/2001 | Kersten et al. |
| 6,401,552 B1 | 6/2002 | Elkins |
| 6,544,424 B1 | 4/2003 | Shevitz |
| 6,544,788 B2 | 4/2003 | Singh |
| 6,582,955 B2 | 6/2003 | Martinez et al. |
| 6,602,711 B1 | 8/2003 | Thomson et al. |
| 7,128,836 B2 | 10/2006 | De Paolis et al. |
| 7,160,719 B2 | 1/2007 | Nyberg |
| 8,785,117 B2 | 7/2014 | Nyberg |
| 2003/0119107 A1 | 6/2003 | Dang et al. |
| 2003/0228685 A1 | 12/2003 | Nyberg |
| 2004/0097867 A1 | 5/2004 | Fraser et al. |
| 2005/0084961 A1 | 4/2005 | Hedrick et al. |
| 2005/0115898 A1 | 6/2005 | Sternby et al. |
| 2006/0019385 A1 | 1/2006 | Smith |
| 2006/0035368 A1 | 2/2006 | Malinge |
| 2008/0014181 A1 | 1/2008 | Ariff et al. |
| 2010/0076380 A1 | 3/2010 | Hui |

FOREIGN PATENT DOCUMENTS

| | | |
|---|---|---|
| CN | 201123923 | 1/2008 |
| CN | 101129276 | 2/2008 |
| CN | 201033178 | 3/2008 |
| EP | 1 063 289 | 12/2000 |
| WO | WO 86/02379 | 4/1986 |
| WO | WO 92/07615 | 5/1992 |
| WO | WO 96/09876 | 4/1996 |
| WO | WO 99/32171 | 7/1999 |
| WO | WO 00/78920 | 12/2000 |
| WO | WO 00/78932 | 12/2000 |

OTHER PUBLICATIONS

Gerlach et al., Hepatocyte aggregate culture technique for bioreactors in hybrid liver support systems. The International Journal of Artificial Organs, vol. 16, No. 12 (1993) pp. 843-846.*

Wheaton Glass Roller Culture Vessels. Datasheet [online]. Fisher Scientific Inc., 2014 [retrieved on Oct. 19, 2015]. Retrieved from the Internet: <URL: https://www.fishersci.com/shop/products/wheaton-glass-roller-culture-vessels-5/p-177149>.*

Akira and Takeda, "Toll-like receptor signaling," *Nat Rev Immunol*, 2004, 4:499-511.

Asano et al., "Ultrastructure of Multicellular Spheroids Formed in the Primary Culture of Adult Rat Hepatocytes," *J. Clin. Electron Microscopy*, 1989, 22(2):243-252.

Brophy et al., "Rat hepatocyte spheroids formed by rocked technique maintain differentiated hepatocyte expression and function," *Hepatology*, 2009, 49:578-586.

Brunn et al., "Conditional signaling by Toll-like receptor 4," *FASEB J*, 2005, 19:872-4.

Busse and Gerlach, "Bioreactors for Hybrid Liver Support: Historical Aspects and Novel Designs," *Ann. N.Y. Acad. Sci.*, 1999, 875:326-339.

(Continued)

*Primary Examiner* — Kara Johnson

(74) *Attorney, Agent, or Firm* — Fish & Richardson P.C.

(57) ABSTRACT

A bioartificial liver system is described that incorporates a cell reservoir and hepatocyte spheroids to both increase the number of and longevity of cells in the system. Additional methods are also described for forming spheroid aggregates from isolated hepatocytes.

6 Claims, 3 Drawing Sheets

(56) References Cited

OTHER PUBLICATIONS

Carrillo et al., "Multiaggregate Hepatocyte (HP) Spheroids in the Hepato-Cellular Transplant: Structural, Functional and Metabolic Characterization," *Transplantation Proceedings*, 2001, 33:660-661.
Curcio et al., "Mass transfer and metabolic reactions in hepatocyte spheroids cultured in rotating wall gas-permeable membrane system," *Biomaterials*, 2007, 28:5487-5497.
De Bartolo et al., "Long-term maintenance of human hepatocytes in oxygen-permeable membrane bioreactor," *Biomaterials*, 2006, 27:4794-4803.
Hong et al., "Effects of Hydrodynamics on Aggregates Formation, Growth and Metabolism of HEK 293 Cells in Suspension Culture," *Chin. J Biotech.*, Jan. 2006, 22(1):101-106.
Koide et al., "Continued High Albumin Production by Multicellular Spheroids of Adult Rat Hepatocytes Formed in the Presence of Liver-Derived Proteoglycans," *Biochem. Biophys. Res. Comm.* 1989, 161:385-391.
Koide et al., "Formation of Multicellular Spheroids Composed of Adult Rat Hepatocytes in Dishes with Positively Charged Surfaces and under Other Nonadherent Environments," *Exp. Cell Res.*, 1990, 186:227-235.
Kurosawa, "Methods for Inducing Embryoid Body Formation: In Vitro Differentiation System of Embryonic Stem Cells," *J Biosci Bioengineering*, 2007, 103(5):389-398.
Lazar et al., "Extended Liver-Specific Functions of Porcine Hepatocyte Spheroids Entrapped in Collagen Gel," *In Vivo Cell Dev. Biol.*, 1995, 31:340-346.
Lazar et al., "Formation of Porcine Hepatocyte Spheroids for Use in a Bioartificial Liver," *Cell Transplantation*, 1995, 4:259-268.
Leffert and Paul, "Studies on primary cultures of differentiated fetal liver cells," *J Cell Biol*, 1972, 52:559-568.
Mashberg, T., "A Life-Saving Liver Machine," Technology Review, Mar. 28, 2006, 3 pages, retrieved from http://www.technologyreview.com/read_article.aspx?ch=biotech&sc=&id=16637&pg=1.
Matsumura et al., "Hybrid bioartificial liver in hepatic failure: Preliminary clinical report," *Surgery*, 1987, 101:99-103.
Mueller-Klieser, "Three-dimensional cell cultures: from molecular mechanisms to clinical applications," *Am. J. Physiol.*, 1997, 273 (Cell Physiol. 42):C1109-C1123.
Nishikawa et al., "Comparison of Assay Methods for Benzodiazepines in Urine," *Am. J. Clin. Pathol.*, 1997, 107(3):345-352.
Nyberg et al., "Brain lactate by magnetic resonance spectroscopy during fulminant hepatic failure in the dog," *Liver TransplantatNion and Surgery*, 1997, 4:158-165.
Nyberg et al., "Rapid, Large-Scale Formation of Porcine Hepatocyte Spheroids in a Novel Spheroid Reservoir Bioartificial Liver," *Liver Transplantation*, 2005, 11(8):901-910.
Ota et al., "Xenotransplantation of Spheroidal Aggregate-Cultured Hepatocytes," *Trans. Proc.*, 1997, 29:912-913.
Ramm, "Isolation and culture of rat hepatic stellate cells," *J Gastroenterol Hepatol*, 1998, 13:846-851.
Rifkind, "Studies on the interaction between endotoxin and polymyxin B," *J Infectious Dis*, 1967, 117:433-438.
Saito et al., "Transplantation of Spheroidal Aggregate Cultured Hepatocytes into the Rat Spleen," *Trans. Proc.*, 1989, 21:2374-2377.
Sakaguchi et al., "Promotion of Spheroid Asembly of Adult Rat Hepatocytes by Some Factor(s) Present in the Initial 6-Hour Conditioned Medium of the Primary Culture," *Pathobiology*, 1991, 59:351-356.
Sakai et al., "A New Bioartificial Liver Using Porcine Hepatocyte Spheroids in High-Cell-Density Suspension Perfusion Culture: In Vitro Performance in Synthesized Culture Medium and in 100% Human Plasma," *Cell Trans.*, 1999, 8:531-541.
Sauer et al., "Clinical extracorporeal hybrid liver support—phase I study with primary porcine liver cells," *Xenotransplantation*, 2003, 10:460-469.
Seglen, "Preparation of isolated rat liver cells," *Methods Cell Biol.*, 1976, 13:29-83.
Shinji et al. "Glycosaminoglycans Partially Substitute for Proteoglycans in Spheroid Formation of Adult Rat Hepatocytes in Primary Culture," *Cell Structure and Function*, 1988, 13:179-188.
Sielaff et al., "A Technique for Porcine Hepatocyte Harvest and Description of Differentiated Metabolic Functions in Static Culture," *Transplantation*, 1995, 59(10):1459-1463.
Sielaff et al., "Application of a bioartificial liver (BAL) in a new model of acute fulminant hepatitis," *Surgical Forum*, 1993, 44:61-63.
Spiegelberg and Bishop, "Tissue-specific gene expression in mouse hepatocytes cultured in growth-restricting medium," *Mol Cell Biol*, 1988, 8:3338-3344.
Stadlbauer et al., "Artificial Liver Support Systems in the Management of Complications of Cirrhosis," *Seminars in Liver Disease*, 2008, 28(1):96-109.
Strain and Neuberger, "A Bioartificial Liver—State of the Art," *Science*, 2002, 295:1005-1009.
Termeer et al., "Oligosaccharides of hyaluronan are potent activators of dendritic cells," *J Immunol*, 2000, 165:1863-1870.
Valatas et al., "Isolation of rat Kupffer cells: a combined methodology for highly purified primary cultures," *Cell Biol International*, 2003, 27:67-73.
Wu et al., "Entrapment of Hepatocyte Spheroids in a Hollow Fiber Bioreactor as a Potential Bioartificial Liver," *Tissue Engineering*, 1995, 1:29-40.
Yagi et al., "Caspase Inhibition Reduces Apoptotic Death of Cryopreserved Porcine Hepatocytes," *Hepatology*, 2001, 33:1432-1440.
Yin et al., "Derivation, Characterization, and Phenotypic Variation of Hepatic Progenitor Cell Lines Isolated From Adult Rats," *Hepatology*, 2002, 35:315-324.
Notice of Allowance in U.S. Appl. No. 10/164,817, mailed Sep. 6, 2006, 4 pages.
Notice of Allowance in U.S. Appl. No. 11/562,008 mailed Sep. 6, 2013, 8 pages.
Office Action and Search Report in Chinese Application No. 201080019388X dated Nov. 15, 2013, 20 pages.
Office Action in U.S. Appl. No. 10/164,817, mailed Feb. 22, 2006.
Office Action in U.S. Appl. No. 11/562,008, mailed May 21, 2009.
Office Action in U.S. Appl. No. 10/164,817, mailed Jun. 15, 2005.
Office Action in U.S. Appl. No. 10/164,817, mailed Aug. 9, 2006.
Office Action in U.S. Appl. No. 11/562,008, mailed Nov. 3, 2009.
Office Action in U.S. Appl. No. 10/164,817, mailed Dec. 15, 2004.
International Preliminary Report on Patentability in International Application No. PCT/US2010/027203, mailed Sep. 22, 2011, 6 pages.
International Search Report and Written Opinion in International Application No. PCT/US2010/027203, mailed Nov. 2, 2010, 9 pages.
International Search Report and Written Opinion in International Application No. PCT/US2003/17909, mailed Feb. 28, 2005, 6 pages.
Office Action in U.S. Appl. No. 13/256,337, mailed Feb. 1, 2013, 18 pages.
Office Action in U.S. Appl. No. 13/256,337, mailed Jun. 17, 2014, 23 pages.
Office Action in U.S. Appl. No. 13/256,337, mailed Sep. 6, 2013, 23 pages.

\* cited by examiner

BIOARTIFICIAL LIVER SYSTEM

CROSS-REFERENCE TO RELATED APPLICATIONS

This application is a continuation application of U.S. application Ser. No. 11/562,008, filed Nov. 21, 2006, which is a continuation application and claims priority to U.S. application Ser. No. 10/164,817, filed Jun. 7, 2002 (now U.S. Pat. No. 7,160,719). The disclosure of the prior applications are considered part of (and are incorporated by reference in) the disclosure of this application.

STATEMENT AS TO FEDERALLY SPONSORED RESEARCH

This invention was made with government support under DK054042 awarded by the National Institutes of Health. The government has certain rights in the invention.

TECHNICAL FIELD

The invention relates to methods and systems for treating biological fluids.

BACKGROUND

Liver failure is associated with significant morbidity and a mortality rate exceeding 40,000 patients annually in the United States. Liver transplantation is the treatment of choice for patients with liver failure. Liver transplantation, however, has several shortcomings, including a scarcity of donor organs, the need for lifelong immunosuppression following transplantation, and the inability to predict or control organ donation. Although living donation addresses some of these problems, less than 20% of patients waiting for a liver transplant are expected to benefit from such a treatment. In addition, many patients with liver failure are not suitable candidates for transplantation due to age, compromised health, or other contraindications. Further, the problem of finding suitable donor livers is expected to increase as a result of the hepatitis C epidemic affecting over 2 million U.S. citizens. Hepatitis C leads to end-stage liver disease in 5-20% of the known cases. Liver support devices have been used to help sustain patients until an organ is available for liver transplantation. The efficiency of such devices, however, has been limited by a number of environmental and nutrient limitations within the device. Therefore, there is a need for an efficient and effective artificial liver.

SUMMARY

The invention provides a bioartificial liver system with an increased number of hepatocytes and the ability to maintain normal liver metabolism during continuous operation. As a result, systems of the invention can improve the efficiency of ex vivo liver assistance provided to a patient experiencing liver failure. The use of spheroids in systems of the invention also improves the longevity and activity of the hepatocytes, and as a result, increases the potential duration of therapy and the overall effectiveness of ex vivo liver assistance.

In one aspect, the invention features a system for treating a biological fluid (e.g., blood or plasma) from a mammal. The system includes a) a bioreactor that includes a selectively permeable barrier separating a fluid treatment compartment and a cell compartment; b) a cell reservoir in fluid communication with the cell compartment of the bioreactor; and c) a rocking device in contact with the cell reservoir to induce motion in fluid contained in the cell reservoir. The system further can include an access port that provides access to the cell reservoir. The access port can allow a component (e.g., a measuring device) access to a medium in the reservoir. The system can include a plurality of cells (e.g., hepatocyte spheroids) in fluid communication with the cell compartment and the cell reservoir, for treating the biological fluid. The system can include about $1 \times 10^5$ to $10 \times 10^6$ hepatocyte spheroids/mL of cell fluid. The system further can include a plurality of pumps for circulating a cell fluid through the cell compartment and the cell reservoir. The system also can include an ultrafiltration cartridge in fluid communication with the cell compartment and the cell reservoir.

The cell reservoir further can include an oxygenator in contact with the cell reservoir. The cell reservoir further can include a cell fluid inlet and a cell fluid outlet, wherein the cell fluid inlet and the cell fluid outlet allow a cell fluid to flow in or out of the cell reservoir.

The bioreactor further can include a biological fluid inlet and a biological fluid outlet, wherein the biological fluid inlet and outlet permit fluid communication between the fluid treatment compartment and the bloodstream of the mammal. The bioreactor further can include a cell fluid inlet and a cell fluid outlet. The selectively permeable barrier can include a bundle of hollow fibers.

In another aspect, the invention features a method for treating a biological fluid (e.g., blood or plasma) from a mammal. The method includes providing a system, as described above, that contains a cell fluid that includes a plurality of cells (e.g., hepatocyte spheroids) for treating the blood, wherein the cell fluid is in fluid communication with the cell compartment and the cell reservoir; removing the biological fluid from the mammal; introducing the biological fluid into the fluid treatment compartment of the bioreactor; and allowing the biological fluid to flow through and exit the fluid treatment compartment, thereby treating the biological fluid.

In yet another aspect, the invention features a method for treating blood from a mammal that includes providing a system, as described above, that contains a cell fluid including a plurality of cells (e.g., hepatocyte spheroids) for treating the blood, wherein the cell fluid is in fluid communication with the cell compartment and the cell reservoir; placing the fluid treatment compartment in fluid communication with the bloodstream of the mammal; and allowing the blood from the mammal to flow through and exit the fluid treatment compartment, thereby treating the blood.

The invention also features a method of forming spheroid aggregates. The method includes providing a reservoir having a plurality of hepatocytes in a cell medium; and rocking the plurality of hepatocytes at a frequency and for a duration sufficient for spheroid aggregates to form.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

DESCRIPTION OF DRAWINGS

Like reference symbols in the various drawings indicate like elements.

DETAILED DESCRIPTION

Figure 1:
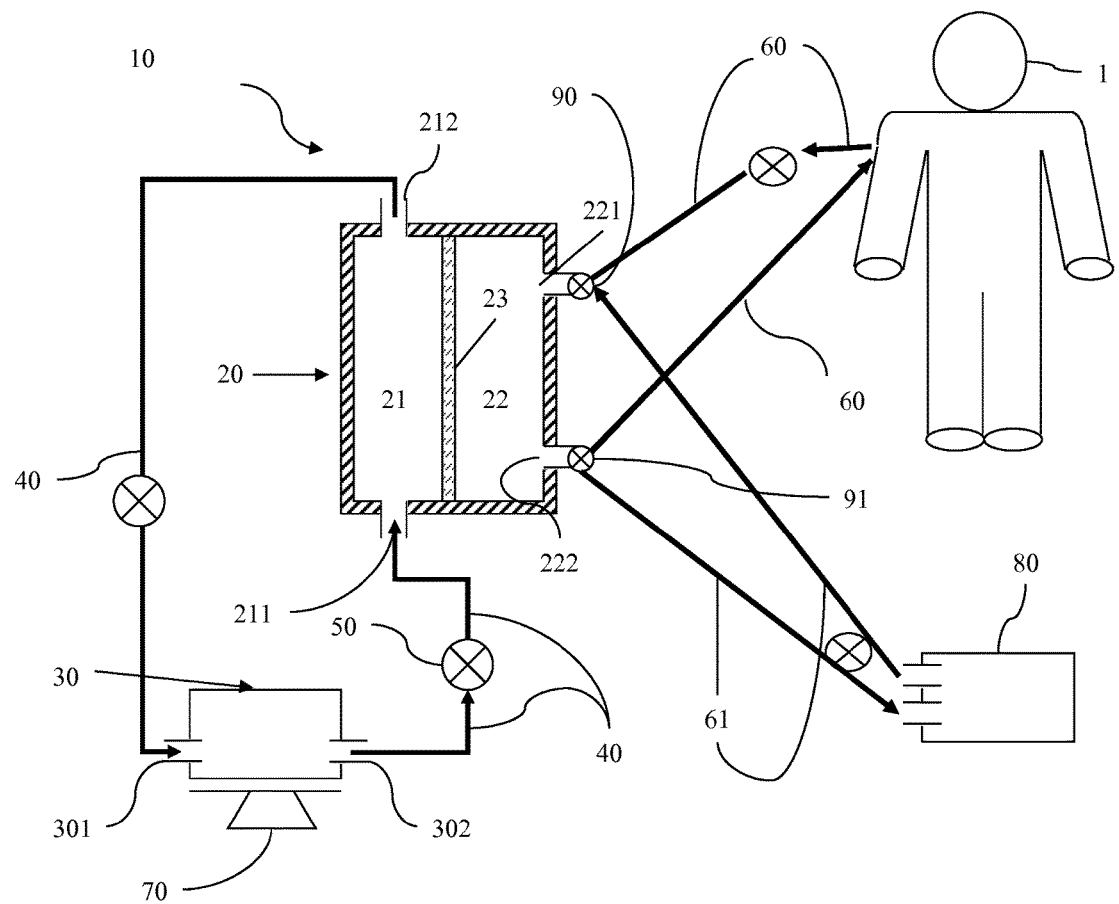
FIG. 1 is a schematic of a bioartificial liver system.

Referring to FIG. 1, an example of a bioartificial liver system 10 in schematic form is shown. In general, system 10 provides a bioartificial liver with increased cell capacity and prolonged metabolic function. As a result, systems of the invention can be used for effective and efficient treatment of a biological fluid from a mammal ex vivo. For example, a mammal with reduced liver function typically exhibits an increase in blood-borne biological waste products as a result of the liver's decreased ability to filter those products from blood. Systems of the invention can assist or replace the liver function of such a mammal by allowing waste products in the bloodstream of the mammal and metabolic products produced by the hepatocytes in system 10 to be transferred to and from hepatocytes circulating within the system, respectively. As used herein, the term "treat" refers to modifying the composition of a biological fluid by removing or adding a component, or by altering the concentration of a component in the biological fluid. Biological fluids that can be treated include, without limitation, blood and plasma.

System 10 includes a bioreactor 20 and a cell reservoir 30 in fluid communication via cell fluid path 40. Bioreactor 20 includes a cell compartment 21 and a fluid treatment compartment 22 separated by a selectively permeable barrier 23. A cell fluid (i.e., isolated cells or multicellular aggregates suspended in an appropriate cell medium) can be introduced into cell compartment 21 via cell fluid inlet 211 and can exit via cell fluid outlet 212. Biological fluid to be treated (e.g., blood or plasma) can be introduced into fluid treatment compartment 22 via biological fluid inlet 221 and can exit via biological fluid outlet 222. For example, a venovenous catheter can be used to place a mammal's bloodstream in fluid communication with fluid treatment compartment 22 via biological fluid path 60. In an alternative embodiment, a biological fluid can be treated in vitro using a biological fluid reservoir (not shown) in place of the mammal. In either case, the biological fluid can enter fluid treatment compartment 22 via biological fluid inlet 221, and exit via biological fluid outlet 222, allowing the biological fluid to return to mammal 1 or to the biological fluid reservoir. Thus, bioreactor 20 operates to bring the biological fluid to be treated in close proximity with the cell fluid so that waste products, for example, may be transferred from the biological fluid to the cell fluid. Although FIG. 1 depicts cell compartment 21 and fluid treatment compartment 22 in a specific orientation (i.e., side-by-side) and having similar dimensions, the compartments can be in any orientation, size, or shape, provided that a selectively permeable barrier 23 separates them. Semipermeable barrier 23 allows small particulates to be exchanged between the cell fluid and biological fluid, while preventing the exchange of large particulates such as cells or antibodies.

Cells (e.g., hepatocyte spheroids) circulating through cell compartment 21 provide the cell fluid with desired particulates, the concentrations of which are high enough to effect their diffusion across selectively permeable barrier 23 into the biological fluid circulating through fluid treatment compartment 22. Because the concentrations of undesired particulates are higher in the biological fluid than in the cell fluid, these undesired particulates diffuse across selectively permeable barrier 23 into the cell fluid, where they can be metabolized by the cells circulating through cell compartment 21 and cell reservoir 30.

Cell reservoir 30 includes a cell fluid inlet 301 for introducing the cell fluid from cell compartment 21 into cell reservoir 30, and a cell fluid outlet 302, which allows the cell fluid to be returned to cell compartment 21. Cell reservoir 30 may allow the system to operate with an increased number of cells at one time. Cell fluid outlet 212 and cell fluid inlet 301, and cell fluid outlet 302 and cell fluid inlet 211 are in fluid communication via tubing (e.g., plastic or stainless steel tubing or pipe). Cell reservoir 30 is in contact with a rocking device 70 (e.g., a platform rocker or rocker plate) which can induce motion in fluid contained in the cell reservoir. In some embodiments, the cell fluid returning to cell compartment 21 is circulated through an ultrafiltration cartridge (not shown) to remove fluid.

Bioreactor 20 and cell reservoir 30 can be constructed out of any of a number of materials, and can be fabricated as a single piece or as multiple pieces joined together, for example, by adhesives or other fasteners.

When preparing to use a bioartificial liver system either ex vivo or in vitro, it may be desirable to precondition or maintain the cell fluid and its accompanying cells. This can be accomplished by placing a media fluid reservoir 80 in fluid communication with fluid treatment compartment 22 of bioreactor 20 via a media fluid path 61. A media fluid reservoir functions similarly to a biological fluid reservoir, except that a preconditioning or maintenance medium is circulated through fluid treatment compartment 22 instead of a biological fluid. The components of the preconditioning or maintenance medium can vary depending on the particular circumstance.

Systems of the invention also can be used for a combination of ex vivo and in vitro applications. For example, as shown in FIG. 1, a system can be connected to a patient and a media fluid reservoir 80 simultaneously. In such cases, fluid-switching devices (e.g., valves) can be included in any fluid path of a system. Fluid-switching devices 90, 91 can be placed at biological fluid inlet 221 and biological fluid outlet 222 to allow the system to switch between media reservoir 80 and the mammal or biological fluid reservoir. In such a case, the media and biological fluid paths can be independently routed through a set of valves such that, using one setting, a biological fluid from the patient can be treated or, using another setting, the cell fluid circulating though the cell compartment of the bioreactor can be reconditioned.

Pumps and sensors can be included to maintain and regulate the fluid flow rate. Pumps 50 are placed in cell fluid path 40, allowing the cell fluid to be circulated from cell compartment 21 through cell reservoir 30. Pumps can be placed at any appropriate point along the circuit defined by cell fluid path 40, cell reservoir 30, and cell compartment 21. For example, as depicted in FIG. 1, pumps 50 can be placed in cell fluid path 40 between cell fluid outlet 212 and cell fluid inlet 301, and between cell fluid outlet 302 and cell fluid inlet 211, allowing a cell fluid to be pumped out of cell reservoir 30 and into cell compartment 21 of bioreactor 20, and back to cell reservoir 30. Although two pumps are depicted in cell fluid path 40 of FIG. 1, it should be appreciated that a single pump can be placed between cell fluid outlet 302 and cell fluid inlet 211 if suitable regulatory controls are placed along the remainder of fluid path 40.

A pump 50 also can be placed along biological fluid path 60 and/or media fluid path 61, allowing a fluid to be circulated through fluid treatment compartment 22 and returned to the mammal or to the media reservoir. A pump can be placed at any appropriate point along the circuit defined by biological fluid path 60 or media fluid path 61, fluid treatment compartment 22, and mammal 1 or media fluid reservoir 80. Pumps suitable to the invention are available commercially, and include, without limitation, syringe pumps, peristaltic pumps, and centrifugal pumps.

Fluid (e.g., cell fluid, biological fluid such as blood or plasma, or media) flow rates suitable to the invention may range from about 10 mL/minute to about 400 mL/minute. The flow rate of the circulating cell fluid should be sufficiently fast such that spheroids do not sediment in the circuit, but not so fast that the cells are disrupted from excess shear forces or that the spheroids are broken up. For example, the flow rate of the circulating cell fluid can be about 10 to 200 mL/minute (e.g., 20 to 80 mL/minute). In the biological fluid circuit, flow rate is limited by physiological concerns. If blood is pumped too slow through the circuit, the blood can separate (i.e., red cells can sediment), but if pumped too fast, the red blood cells can undergo lysis. Maximum blood and plasma removal rates also are limited by the patient's circulatory system. For example, the flow rate of the biological fluid can be about 20 to 400 mL/minute (e.g., 150 to 200 mL/minute). Although FIG. 1 depicts the cell fluid flowing counter-current to the biological fluid or media, co-current flow also can be used. In addition, the cell fluid can be pumped in an alternating counter-current/co-current pattern, which can further prevent cell adhesion in the system (e.g., on the selectively permeable barrier) and can aid in mixing or dispersing particulates within or between cell compartment 21 and fluid treatment compartment 22 of bioreactor 20.

Each component in the system can be configured with appropriate hardware such that the components can be in fluid communication with one or other components. In addition, each component can be configured with hardware for controlling fluid flow. Thus, each component in the system may contain, for example, clamps, valves, gaskets, or joints on inlet and/or outlet ports.

The temperature of fluids circulating through the system can be maintained at or about human body temperature (about 37° C.) using external temperature controls (not shown). Alternatively, components of the system can be contained within a temperature-controlled housing.

Selectively Permeable Barriers

Selectively permeable barrier 23 can be any semi-permeable membrane that allows small particulates to be exchanged between cell compartment 21 and fluid treatment compartment 22, while preventing large particulates from being exchanged. Small particulates include, without limitation, gases (e.g., carbon dioxide, oxygen, nitrogen, argon, and helium), solutes (e.g., sodium chloride and sodium bicarbonate), toxins (e.g., aminated molecules), proteins (e.g., albumin), metabolic products (e.g., urea and conjugated bilirubin) and biological waste products (e.g., ammonia). Large particulates include, without limitation, cells and antibodies. Typically, the porosity of selectively permeable barrier 23 is at least about 70 kD (e.g., 70 kD to 100 kD or 100 kD to 150 kD).

Typically, bioreactor 20 and selectively permeable barrier 23 are configured to include one or more self-supporting hollow fiber bundles (i.e., a hollow fiber bioreactor) having a high surface area to volume ratio. Each hollow fiber within the bundle is a tubular barrier having a small diameter (e.g., 170 µm to 1 mm or 200 to 500 µm). The hollow fiber bundles may be contained within a housing made of a biocompatible material.

Figure 2:
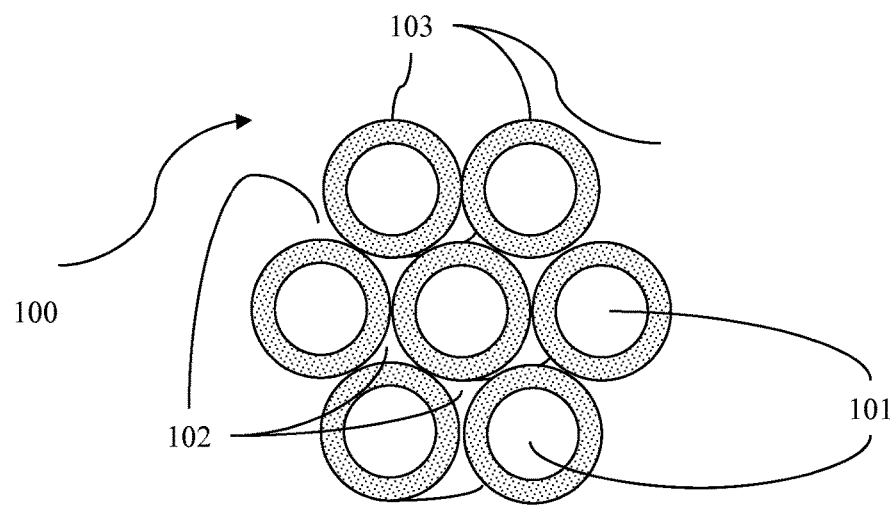
FIG. 2 is a schematic of a hollow fiber bundle.

FIG. 2 depicts, in cross-section, hollow fiber bundle 100, which includes intracapillary space 101 and extracapillary space 102 separated by selectively permeable barrier 103. Either of intracapillary space 101 or extracapillary space 102 can be used as a cell compartment in bioreactor 20. For example, intracapillary space 101 of hollow fiber bundle 100 can be placed in fluid communication with cell reservoir 30 via cell fluid path 40. In such a case, intracapillary space 101 would be cell compartment 21 and extracapillary space 102 would be fluid treatment compartment 22 of bioreactor 20. Alternatively, extracapillary space 102 of hollow fiber bundle 100 can be placed in fluid communication with cell reservoir 30 via cell fluid path 40. In such a situation, extracapillary space 102 would be cell compartment 21 and intracapillary space 101 would be fluid treatment compartment 22. Hollow fiber bioreactors, such as those just described are available commercially from manufacturers such as Spectrum Labs (Rancho Dominguez, Calif.), Toray Industries, Inc. (Tokyo, Japan), Minntech Corporation (Minneapolis, Minn.), Althin Medical (Ronneby, Sweden), Baxter (Deerfield, Ill.), and Asahi Medical Co. (Northbrook, Ill.).

Cell Reservoirs

Figure 3:
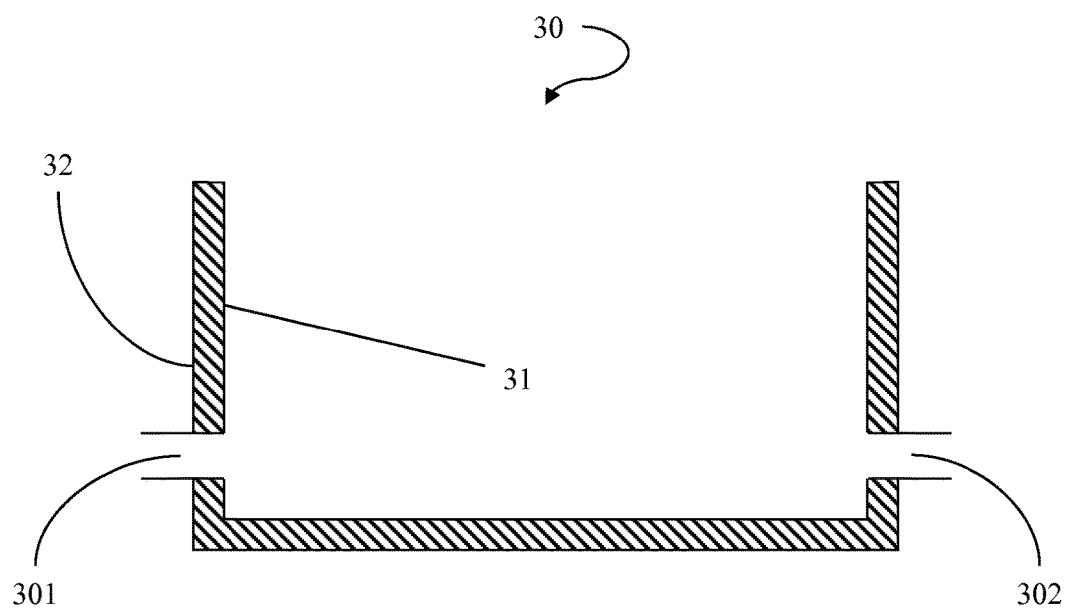
FIG. 3 is a schematic of a cell reservoir.

Referring to FIG. 3, cell reservoir 30 may allow the system to operate with an increased number of cells at one time. Cell reservoir 30 includes inner surface 31 and outer surface 32. Inner surface 31, which is in contact with the cell fluid, typically is made of a material that prevents cells in the cell fluid from adhering to the reservoir. Suitable materials include typical tissue culture materials such as glass or plastic (e.g., polystyrene, polypropylene or polyethylene). Inner surface 31 also can be coated, for example, with silicone to prevent the cells from adhering to the inner surface. Alternatively, the entire reservoir (i.e., the inner and outer surfaces and any material in between) can be composed of the same material. For example, the entire reservoir can be composed of glass. Further, an electric charge (e.g., a positive charge) can be imparted to the inner surface or the entire reservoir to prevent cells from adhering to the reservoir. The reservoir can be of any appropriate shape, including, for example, cylindrical, spherical, or cubical.

Additional components can be optionally included in cell reservoir 30 to provide process control (i.e., for monitoring or altering system performance) when using the system. Non-limiting examples of process controls that can be incorporated into the system include measurement devices, automated syringes, and devices for delivering oxygen (e.g., an oxygenator membrane). Measurement devices can be used to measure pH (e.g., a pH probe), $O_2$ (e.g., an $O_2$ sensor or probe), hepatocyte substrates such as lactate or amino acids, hepatocyte products such as glucose, nutrients, waste products, pressure, or temperature (e.g., a thermometer or temperature probe).

Figure 4:
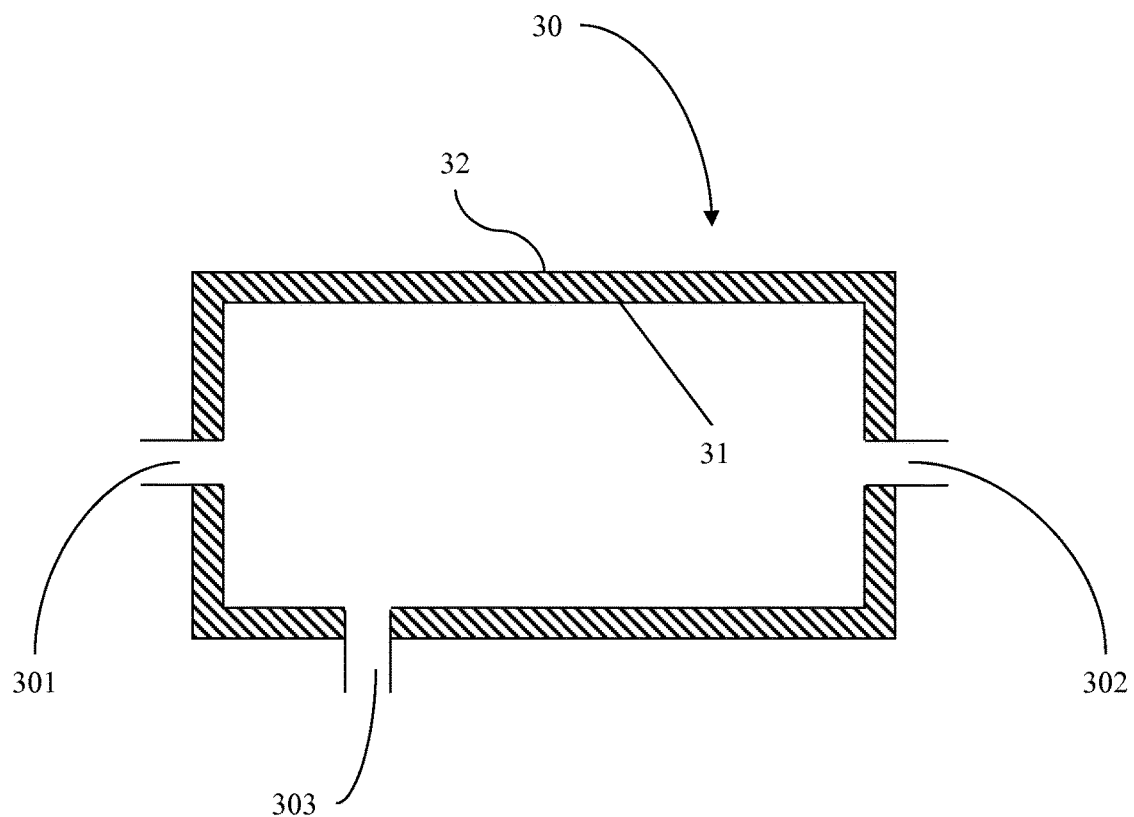
FIG. 4 is a schematic of the top view of a cell reservoir with an access port.

FIG. 4 shows a cross section view of cell reservoir 30. As shown in FIG. 4, a process control component can access the cell fluid circuit of the system via access port 303 in cell reservoir 30. Additional access ports can be provided to allow multiple process control components simultaneous access to the cell fluid. It is noted that access port 303 can be located at any appropriate place in the system, including in cell fluid path 40 or in bioreactor 20 as depicted in FIG. 1, to allow access to the cell fluid. In addition, a series of access ports, each providing a process control component access to the cell fluid, can be located throughout the system. An access port also can be used to remove a sample from the system for testing.

Cells Contained within the Cell Compartment and Cell Reservoir

Typically, the cells circulating through cell compartment 21 and cell reservoir 30 are hepatocytes, the principal cells of the liver, which are capable of producing desired particulates or metabolizing undesired particulates related to liver function when placed in an appropriate chemical and structural environment. Other cells present in the liver also can be included in the system such as endothelial cells, Ito cells, Kupffer cells, and fibroblasts. A co-culture of hepatocytes with one or more of these or other types of cells also can be used in a bioartificial liver system.

Hepatocytes can be obtained from mammalian livers, including, without limitation, human, equine, canine, porcine, bovine, ovine, and murine sources. Typically, when treating a biological fluid from a human, hepatocytes from human donors are desired. Cell donors can vary in development and age, gender, species, weight, and size. Cells can be derived from donor tissues of embryos, neonates, or older individuals including adults. Hepatocytes can be obtained using standard techniques. See, for example, Sielaff et al., *Transplantation* 59:1459-1463 (1995). Freshly isolated hepatocytes can be used, as well as hepatocytes that have been cryopreserved.

Hepatic stem cells also can be used in systems of the invention. Hepatic stem cells can be isolated according to the method of Yin et al., *Hepatology* 35:315-324 (2002). Embryonic progenitor cells such as parenchymal or mesenchymal stem cells also can be induced to differentiate into the desired cell type and used in the invention.

In addition, mixtures of cells from different cell strains, mixtures of normal and genetically modified cells, or mixtures of cells from two or more species or tissue sources may be used for treating patients with liver failure. Cells for use in the invention can be genetically modified using, without limitation, spontaneous, chemical, or viral methods. Genetically modified cells can exhibit characteristics such as immortality, reduced allogenicity, or differentiated hepatocyte function. Methods for genetically modifying cells are generally known in the art, and are described in Sambrook et al., Molecular Cloning, A Laboratory Manual, Cold Spring Harbor Press, Cold Spring Harbor, N.Y. (1989).

In some embodiments, hepatocytes are present as spheroids, multicellular aggregates that exhibit a more tissue-like morphology and function. Spheroids create an environment for the hepatocytes, such that the hepatocytes can maintain function closer to that of an intact liver. As a result, using spheroids can improve the longevity of the cells and the system, as well as the efficiency and effectiveness of treating biological fluids. Thus, metabolic activity can be improved during continuous operation of the system.

The present invention provides a method for forming spheroids that allows aggregates to be formed rapidly. As described herein, spheroids can be formed by rocking cells at a frequency and for a duration sufficient for spheroid aggregates to form. For example, cell reservoir 30 can be placed in contact with the upper surface of a rocking device 70 (depicted in FIG. 1) adjusted to rock at a specified frequency (e.g., 6 hertz) and elevation (e.g., 20°). The cells are agitated until spheroids form, a period that can vary with cell density. As described herein, when $0.5-5\times10^7$ cells/mL were used, spheroids formed after approximately 12-24 hours of agitation. Advantageously, using the methods of the invention, spheroids can form in the absence of added proteoglycans and glycosaminoglycans, and in less than 24 hours.

Spheroids also can be formed by methods described in the following references: Lazar, A. et al., *Cell Trans.*, 4:259-268 (1995); Lazar, A., et al., *In vitro Cell Dev. Biol.*, 31:340-346 (1995); Sakai, Y, et al., *Cell Trans.*, 8:531-541 (1999); Wu, F. et al., *Tissue Eng.*, 1:29-40 (1995); Saito, S. et al., *Trans. Proc.*, 21:2374-2377 (1989); Carrillo, G. et al., *Trans. Proc.*, 33:660-661 (2001); Shinji, T. et al., *Cell Structure and Function*, 13:179-188 (1988); Koide, N. et al., *Exper. Cell Res.*, 186:227-235 (1990); and Yada, T. et al. (U.S. Pat. No. 5,624,839).

As noted earlier, the presence of cell reservoir 30 in fluid communication with cell compartment 21 via cell fluid path 40, allows the overall number of cells in system 10 to be greatly increased. The number of cells in a system can range from about $1\times10^7$ cells to about $1\times10^8$ cells per mL of cell fluid (e.g., $1.0\times10^7$ cells to $10.0\times10^7$ cells and $3.0\times10^7$ cells to $7.0\times10^7$ cells per mL of cell fluid). Cell fluid volume can range from about 500 mL to about 5000 mL (e.g., 1000 mL to 3000 mL). Typically, a system includes about $5\times10^7$ cells per mL of cell fluid in a cell fluid volume of about 2000 mL to achieve from about 500 grams to about 1000 grams of cells for treating an adult human patient.

Spheroids can be formed before their introduction into the system, or can be formed from isolated cells that are introduced into the system using the rocking device that is in contact with the cell reservoir. If about $10^7$-$10^8$ hepatocytes/mL of cell medium are introduced into the cell reservoir, about $10^5$-$10^6$ hepatocyte spheroids/mL of cell medium can be formed since spheroids vary in size, but, on average, contain about 100 hepatocytes/spheroid. Inclusion of a rocking device in systems of the invention also can help to maintain the cells as spheroids as the spheroids are being circulated through the system.

To determine if cells (e.g., spheroids) are suitable for a system of the invention, the viability and metabolic efficiency of the spheroids can be determined. Viability can be determined using methods known in the art, such as Trypan blue exclusion. Metabolic efficiency can be determined by measuring, without limitation, albumin production, diazepam metabolism, and urea production (i.e., ureagenesis). Albumin production can be determined using an ELISA method. See, Yagi et al., *Hepatology*, 33:1432-1440 (2001). Diazepam metabolism can be determined using a gas chromatography/mass spectroscopy technique. In this method, diazepam (5 mg/ml) can be added to the culture media. The concentrations of diazepam and its three major metabolites can be determined in samples of culture media after 24 hr by gas chromatography with mass spectroscopy detection (GC system 6890 and Mass Selective Detector 5973, Hewlett Packard, St. Paul, Minn.) using a method adapted from Nishikawa et al. (Nishikawa et al., *Am. J. Clin. Pathol.* 107:345-52 (1997). Urea production can be assessed using a commercially available kit (e.g., #535A, Sigma Diagnostics, St. Louis, Mo.) or can be assessed using mass spectroscopy. The Sigma kit uses a colorimetric assay based on the reaction of urea and diacetylmonoxime. Samples of media (100 µL) can be analyzed spectrophotometrically (570 nm) as specified in the kit's instructions.

Kits

Components of a bioartificial liver system can be provided in a kit. Examples of such components include, without limitation, bioreactors (e.g., hollow fiber bundle bioreactors), cell reservoirs, biological fluid reservoirs, media fluid reservoirs, and tubing. In addition, kits can include process control components such as measurement devices or oxygen delivering devices. Kits also can include cells and a suitable cell fluid (e.g., a medium suited for the growth and maintenance of the particular type of cells). In one embodiment, a kit can include a bioreactor having a selectively permeable barrier separating a fluid treatment compartment and a cell compartment, a cell reservoir with an inner surface that prevents cells from adhering to the reservoir, and tubing for placing the cell compartment of the bioreactor in fluid communication with the cell reservoir.

The invention will be further described in the following example, which does not limit the scope of the invention described in the claims.

EXAMPLE

Generating Spheroid Aggregates

Hepatocytes were isolated from livers using a collagenase perfusion technique similar to the two-step technique reported for obtaining pig hepatocytes. See, Sielaff T. D. et al., *Transplantation* 59:1459-1463 (1995). Hepatocytes were used fresh or cryopreserved in liquid nitrogen at $-80°$ C. for at least one week before being used for spheroid formation. To form spheroids, hepatocytes were first resuspended in William's E medium supplemented with 10% fetal bovine serum, 2 mmol/L L-glutamine, 15 mmol/L HEPES, 1.5 mg/L insulin, 10,000 U/L penicillin G, 100 mg/L streptomycin, and pH (7.4). Hepatocyte suspensions (0.5, 1, 2, or $5 \times 10^7$ cells/mL) were transferred to ten flat (T75 cm$^2$) culture flasks, with each flask containing 20 mL medium. Each culture flask was then placed in an incubator at 37° C. and agitated on a rocker plate with a frequency of 6 hertz and a maximum elevation of 20°. Controls included monolayer and collagen gel cultures cultured under static, yet otherwise identical, conditions. After 1, 3, or 5 days, hepatocyte activity was determined by measuring albumin production in the culture media by ELISA. See, Yagi T. et al., *Hepatology* 33:1432-1440 (2001). Ureagenesis and diazepam metabolism also was assessed as described below. ANOVA and Student's t-test were used to determine significance.

The specific activity of pig hepatocytes in the spheroid culture increased with time compared to the monolayer culture or the collagen gel culture (Table 1). At culture day 1, albumin production was similar across the different culture conditions. At culture day 3, albumin production in the spheroid culture was 21.8 µg/hr/$10^8$ cells, almost twice the amount measured in either the monolayer culture (10.1 µg/hr/$10^8$ cells) or the collagen gel culture (12.1 µg/hr/$10^8$ cells). By culture day 5, albumin production was greatly increased in the spheroid culture (32.7 µg/hr/$10^8$ cells) compared to either the monolayer culture (4.1 µg/hr/$10^8$ cells) or the collagen gel culture (14.7 µg/hr/$10^8$ cells).

TABLE 1

Hepatocyte function in spheroid aggregates
Albumin Production (µg/hr/$10^8$ cells)

| Culture day | Spheroid culture mean | Monolayer culture Mean | p* | Collagen gel culture mean | p* |
|---|---|---|---|---|---|
| 1 | 7.6 | 7.2 | 0.37176 | 8.2 | 0.08152 |
| 3 | 21.8 | 10.1 | 0.00002 | 12.1 | 0.00041 |
| 5 | 32.7 | 4.1 | 0.00000 | 14.7 | 0.00132 |

*p values represent significance relative to spheroid culture mean

Ureagenesis was assessed in spheroids and monolayer cultures of human hepatocytes, which were isolated from a fatty discarded human liver (not suitable for liver transplantation). Mass spectroscopy was used to measure ureagenesis by following the conversion of heavy ammonia (N15D3) into heavy urea. Intact urea cycle activity could only be detected in the cultures containing spheroids.

Diazepam metabolism was assessed in spheroid and monolayer cultures of both fresh and cryopreserved pig hepatocytes, by measuring oxazepam formation, a metabolite of diazepam. Hepatocytes were cryopreserved using a global caspase inhibitor. See, Yagi et al., *Hepatology* 33:1432-1440 (2001). Spheroids from both fresh hepatocytes (FS) and cryopreserved hepatocytes (CS) had significantly greater (p<0.0001) diazepam elimination rates than monolayer cultures of fresh pig hepatocytes (FM). In fact, spheroids from cryopreserved porcine hepatocytes were metabolizing diazepam as well, if not better, than the spheroids from fresh pig hepatocytes by day 5 in culture. See Table 2.

These data demonstrate that spheroid aggregates of hepatocytes exhibit increased metabolic activity compared to hepatocytes cultured as monolayers. These data also demonstrate that spheroid aggregates of hepatocytes are suitable for continuous operation of a spheroid hepatocyte bioartificial liver.

TABLE 2

Oxazepam Formation on Day 5 of culture (ng/mL/$10^6$ cells)

| Group | mean | St. dev. | P value vs. FM |
|---|---|---|---|
| CS | 50.1 | 3.4 | 0.00004 |
| FS | 42.3 | 12.2 | 0.018 |
| FM | 24.2 | 6.2 | — |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of forming spheroid aggregates, said method comprising:
    a) providing a reservoir having a plurality of hepatocytes in fluid; and
    b) rocking said plurality of hepatocytes at a frequency and for a duration sufficient for spheroid aggregates to form using a rocking device that is the sole device for imparting motion on said reservoir.

2. The method of claim 1, wherein said reservoir comprises $0.5 \times 10^7$ to $5 \times 10^7$ hepatocytes/mL of said fluid.

3. The method of claim 1, wherein said hepatocytes are human hepatocytes.

4. The method of claim 1, wherein said reservoir comprises between about 500 mL to about 5000 mL of said fluid.

5. The method of claim 1, wherein said reservoir comprises between about 1000 mL to about 3000 mL of said fluid.

6. The method of claim 1, wherein said duration is from about 12 hours to about 24 hours.

* * * * *